United States Patent [19]

Fisher et al.

[11] Patent Number: 5,783,731
[45] Date of Patent: Jul. 21, 1998

[54] REMOVAL OF CARBONYL IMPURITIES FROM A CARBONYLATION PROCESS STREAM

[75] Inventors: Darrell Andrew Fisher; Michael L. Karnilaw, both of Houston; Kenneth Paul Kidwell, League City; Melchior Albert Meilchen, Corpus Christi; Valerie Santillan, Webster; Mark O. Scates, Friendswood; G. Paull Torrence, Corpus Christi; Richard F. Vogel, Jr., League City; R. Jay Warner, Corpus Christi, all of Tex.

[73] Assignee: Hoechst Celanese Corporation, Somerville, N.J.

[21] Appl. No.: 526,338

[22] Filed: Sep. 11, 1995

[51] Int. Cl.$^6$ ........................................ C07C 51/12
[52] U.S. Cl. ........................................ 562/519
[58] Field of Search ........................................ 562/519

[56] References Cited

U.S. PATENT DOCUMENTS

| | | |
|---|---|---|
| 2,126,611 | 8/1938 | Britton . |
| 2,862,854 | 12/1958 | MacLean . |
| 5,001,259 | 3/1991 | Smith et al. ............... 562/519 |
| 5,371,286 | 12/1994 | Blay et al. ............... 562/519 |
| 5,374,774 | 12/1994 | Ochiai ............... 562/519 |

FOREIGN PATENT DOCUMENTS

| | | | |
|---|---|---|---|
| 161 874 B2 | 11/1985 | European Pat. Off. | ........ C07C 53/08 |
| 487 284 B1 | 5/1992 | European Pat. Off. | ........ C07C 51/12 |
| 497 521 A2 | 8/1992 | European Pat. Off. | ........ C07C 53/08 |
| 61-56151 | 3/1986 | Japan | ........ C07C 53/08 |
| 4-338357 | 11/1992 | Japan | ........ C07C 53/08 |

*Primary Examiner*—C. Warren Ivy
*Assistant Examiner*—Jean F. Vollano
*Attorney, Agent, or Firm*—M. Susan Spiering

[57] ABSTRACT

A process to reduce carbonyl impurities in a carbonylation reaction for the production of acetic acid is described. The methyl iodide recycle stream which is directed to a carbonylation reactor for carbonylating methanol or methyl acetate to acetic acid, is treated to remove carbonyl impurities by reacting the methyl iodide stream formed in the reaction with an aqueous amino compound which reacts with the carbonyls to form water soluble nitrogenous derivatives, separating an organic methyl iodide phase from an aqueous derivative phase and distilling the methyl iodide phase to remove heavier impurities. The treatment of the methyl iodide recycle stream to the carbonylation reactor has been found to greatly reduce the carbonyls present in the acetic acid product. The formation of nitrile from the nitrogenous derivative during distillation may be minimized by adding water to the system.

13 Claims, 2 Drawing Sheets

REMOVAL OF CARBONYL IMPURITIES FROM A CARBONYLATION PROCESS STREAM

FIELD OF INVENTION

This invention relates to a novel process for the purification of acetic acid formed by the carbonylation of methanol in the presence of a Group VIII metal carbonylation catalyst. More specifically, this invention relates to a novel process for reducing or removing carbonyl impurities from acetic acid formed by Group VIII metal-catalyzed, carbonylation processes.

BACKGROUND

Among currently-employed processes for synthesizing acetic acid one of the most useful commercially is the catalyzed carbonylation of methanol with carbon monoxide as taught in U.S. Pat. Nos. 3,769,329 issued to Paulik et al on Oct. 30, 1973. The carbonylation catalyst comprises rhodium, either dissolved or otherwise dispersed in a liquid reaction medium or else supported on an inert solid, along with a halogen-containing catalyst promoter as exemplified by methyl iodide. The rhodium can be introduced into the reaction system in any of many forms, and it is not relevant, if indeed it is possible, to identify the exact nature of the rhodium moiety within the active catalyst complex. Likewise, the nature of the halide promoter is not critical. The patentees disclose a very large number of suitable promoters, most of which are organic iodides. Most typically and usefully, the reaction is conducted with the catalyst being dissolved in a liquid reaction medium through which carbon monoxide gas is continuously bubbled.

An improvement in the prior-art process for the carbonylation of an alcohol to produce the carboxylic acid having one carbon atom more than the alcohol in the presence of a rhodium catalyst is disclosed in commonly assigned U.S. Pat. Nos. 5,001,259, issued Mar. 19, 1991; 5,026,908, issued Jun. 25, 1991 and 5,144,068, issued Sep. 1, 1992 and European patent 161,874 B2, published Jul. 1, 1992. As disclosed therein acetic acid is produced from methanol in a reaction medium comprising methyl acetate, methyl halide, especially methyl iodide, and rhodium present in a catalytically-effective concentration. The invention therein resides primarily in the discovery that catalyst stability and the productivity of the carbonylation reactor can be maintained at surprisingly high levels, even at very low water concentrations, i.e. 4 weight (wt) % or less, in the reaction medium (despite the general industrial practice of maintaining approximately 14 wt % or 15 wt % water) by maintaining in the reaction medium, along with a catalytically-effective amount of rhodium, at least a finite concentration of water, methyl acetate and methyl iodide, a specified concentration of iodide ions over and above the iodide content which is present as methyl iodide or other organic iodide. The iodide ion is present as a simple salt, with lithium iodide being preferred. The patents teach that the concentration of methyl acetate and iodide salts are significant parameters in affecting the rate of carbonylation of methanol to produce acetic acid especially at low reactor water concentrations. By using relatively high concentrations of the methyl acetate and iodide salt, one obtains a surprising degree of catalyst stability and reactor productivity even when the liquid reaction medium contains water in concentrations as low as about 0.1 wt %, so low that it can broadly be defined simply as "a finite concentration" of water. Furthermore, the reaction medium employed improves the stability of the rhodium catalyst, i.e. resistance to catalyst precipitation, especially during the product-recovery steps of the process wherein distillation for the purpose of recovering the acetic acid product tends to remove from the catalyst the carbon monoxide which in the environment maintained in the reaction vessel, is a ligand with stabilizing effect on the rhodium. U.S. Pat. Nos. 5,001,259; 5,026,908 and 5,144,068 are herein incorporated by reference.

The acetic acid which is formed by the carbonylation of methanol is converted to a high purity product by conventional means such as by a series of distillations. While it is possible in this way to obtain acetic acid of relatively high purity, the acetic acid product formed by the above-described low water carbonylation is frequently deficient with respect to the permanganate time owing to the presence therein of small proportions of residual impurities. Since a sufficient permanganate time is an important commercial test which the acid product must meet for many uses, the presence therein of such impurities that decrease permanganate time is objectionable. The removal of minute quantities of these impurities from the acetic acid by conventional distillation techniques is not commercially feasible.

Among the impurities which decrease the permanganate time of the acetic acid are carbonyl compounds, unsaturated carbonyl compounds, and organic iodides. As used herein, the phrase "carbonyl" is intended to mean compounds which contain aldehyde or ketone functional groups which compounds may or may not possess unsaturation. It has been found that during the production of acetic acid by the carbonylation of methanol or methyl acetate in the presence of a finite amount of water, carbonyl impurities such as acetaldehyde, acetone, methyl ethyl ketone, butyraldehyde, crotonaldehyde, 2-ethyl crotonaldehyde, and 2-ethyl butyraldehyde and the like, are present and may further react to form aldol condensation products and/or react with iodide catalyst promoters to form multi-carbon alkyl iodides, i.e., ethyl iodide, butyl iodide, hexyl iodide and the like.

Unfortunately, it is difficult to completely remove the minor amounts of carbonyl impurities which are present by conventional means such as distillation inasmuch as the impurities have boiling points close to that of the acetic acid product. It is known to remove carbonyl impurities, in general, from organic streams by treating the organic streams with an amine compound such as hydroxylamine which reacts with the carbonyl compounds to form oximes followed by distillation to separate the purified organic product from the oxime reaction products. However, the additional treatment of the final product adds cost to the process and it has been found that distillation of the treated acetic acid product can result in additional impurities being formed. For example, it has been found that the formation of nitriles from the oximes readily occurs during distillation to remove the oximes. Obviously, if the final product is again contaminated, such process is not readily useful.

Thus, while removing carbonyl impurities from the acetic acid carbonylation product, it has been found to be of critical importance in yielding a pure product to determine where in the carbonylation process such impurities can be removed and by what process without risk of further contamination.

In EP 487,284, B1, published Apr. 12, 1995, there is disclosed a process to minimize the amount of circulating carbonyl-containing organic materials and unsaturated organic materials in the carbonylation reaction mixture, resulting in a more facile purification of acetic acid, which acetic acid has been formed by the carbonylation of methanol in the presence of a Group VIII metal carbonylation catalyst under the low water carbonylation conditions such as set forth in U.S. Pat. No. 5,001,259. In such processes, a feed of methanol is carbonylated in a liquid phase carbonylation reactor. Separation of products is achieved by directing the contents of a reactor to a flasher wherein the catalyst solution is withdrawn as a base stream and recycled to the reactor while the vapor or volatile overhead which comprises largely the product acetic acid along with methyl iodide, methyl acetate, and water is directed to a methyl iodide-acetic acid splitter column. The overhead from the splitter column comprises mainly organic iodides, methyl acetate, acetic acid, and water, whereas from near the base of the splitter column is drawn the crude acetic acid which is usually directed to further purification by finishing distillation. The overhead from the splitter column containing the organic iodides is recycled to the carbonylation reactor. It was discovered that the carbonyl impurities present in the acetic acid product generally concentrate in the overhead from the splitter column. In accordance with the process disclosed in EP 487,284, the splitter column overhead is treated with a compound i.e., hydroxylamine which reacts with the carbonyl compounds to allow such carbonyls to be separated from the remaining overhead by means of distillation. Modified by such a treatment, the carbonylation of methanol yields an acetic acid product which has greatly improved permanganate time and is substantially free from carbonyl impurities.

While the above-described process has been successful in removing carbonyl impurities from the carbonylation system and for the most part controlling acetaldehyde levels and permanganate time problems in the final acetic acid product, improvements can still be made. Accordingly, there remains a need to determine where in the carbonylation process the carbonyl materials can be removed so as to insure consistent purity of product and at the same time, provide a process for removal of such carbonyl materials without sacrificing the productivity of the low water carbonylation process or without incurring substantial additional energy costs.

SUMMARY OF THE INVENTION

It has now been found that vent gas from the splitter column overhead receiver decanter (which contains a portion of the condensed splitter column overhead gases) contains a substantial concentration of acetaldehyde and if this vent gas is further condensed and the condensate containing the high concentration of acetaldehyde is treated with an amino compound to remove the carbonyl compounds therefrom, the inventory of acetaldehyde throughout the carbonylation reaction system is even more greatly reduced. In one aspect of this invention, the condensate from the vent gas is treated directly with an amino compound to remove carbonyl impurities. In another aspect of the present invention, the condensate is combined with a small slipstream from the condensed splitter column overhead to be treated with an amino compound to remove the carbonyl compounds. The bulk of the overhead receiver decanter is recycled to the reactor. Thus, in accordance with the present invention, the inventory of carbonyl compounds including acetaldehyde is greatly reduced by treating only minor amounts of the production streams of the carbonylation process, achieving greatly improved product quality and, at the same time, accomplishing such product quality without substantially increasing the cost of production.

In a process for the carbonylation of methanol to a product of acetic acid, said methanol is carbonylated in a suitable liquid phase reaction medium comprising a Group VIII metal catalyst, an organic iodide and iodide salt catalyst promoter; the products of said carbonylation separated into a volatile phase comprising product, and a less volatile phase comprising Group VIII metal catalyst, acetic acid, iodide catalyst promoter, and organic iodide; said product phase distilled in a distillation tower to yield a purified product and an overhead comprising organic iodide, methyl acetate, water, acetic acid, and unreacted methanol, and recycling said overhead to said carbonylation reactor, the improvement which comprises (a) directing at least a portion of the overhead to an overhead receiver which separates the overhead into a light phase, comprising acetic acid and water, and a heavy phase comprising methyl acetate and organic iodide;
(b) venting a gas stream from the overhead receiver of (a);
(c) chilling the vented gas stream of (b) under suitable conditions to condense and separate said condensable phase from noncondensable light gases;
(d) contacting the condensable phase of (c) with an aqueous amino compound which forms water soluble nitrogenous derivatives of carbonyls;
(e) separating out resulting nitrogenous derivatives of carbonyl compounds and returning a purified condensable phase of (c) to the carbonylation reactor.

DRAWINGS

DETAILED DESCRIPTION

Figure 1:
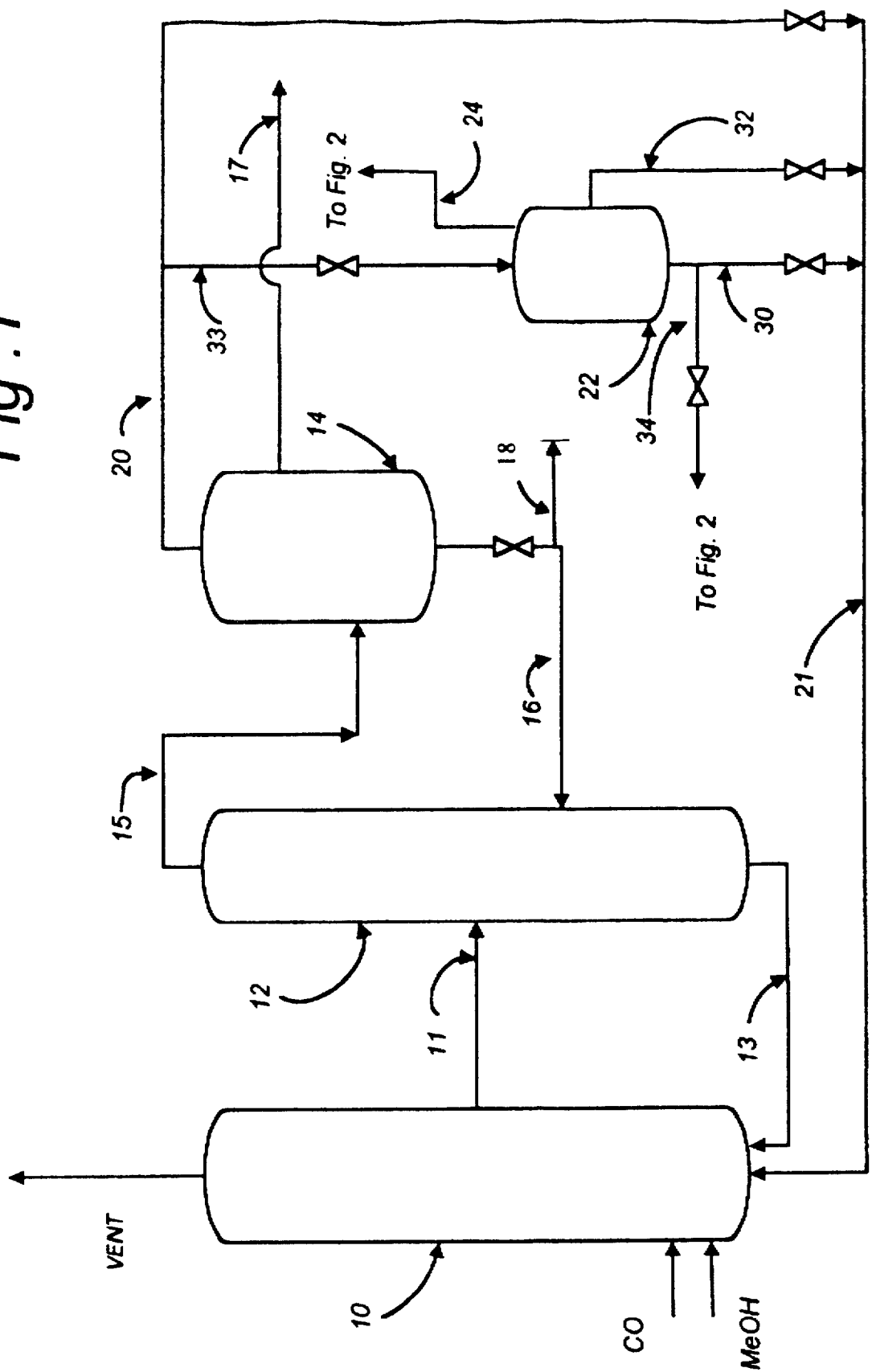
FIG. 1 illustrates a carbonylation reaction process and acetic acid recovery system as modified to provide for the incorporation of the present invention.

The purification process of the present invention is useful in any process used to carbonylate methanol to acetic acid in the presence of a Group VIII metal catalyst such as rhodium and an iodide promoter. A particularly useful process is the low water rhodium catalyzed carbonylation of methanol to acetic acid as exemplified in aforementioned U.S. Pat. No. 5,001,259. Generally, the rhodium component of the catalyst system is believed to be present in the form of a coordination compound of rhodium with a halogen component providing at least one of the ligands of such coordination compound. In addition to the coordination of rhodium and halogen, it is also believed that carbon monoxide ligands form coordination compounds or complexes with rhodium. The rhodium component of the catalyst system may be provided by introducing into the reaction zone rhodium in the form of rhodium metal, rhodium salts and oxides, organic rhodium compounds, coordination compounds of rhodium, and the like.

The halogen promoting component of the catalyst system consists of a halogen compound comprising an organic halide. Thus, alkyl, aryl, and substituted alkyl or aryl halides can be used. Preferably, the halide promoter is present in the form of an alkyl halide in which the alkyl radical corresponds to the alkyl radical of the feed alcohol which is carbonylated. Thus, in the carbonylation of methanol to acetic acid, the halide promoter will comprise methyl halide, and more preferably methyl iodide.

The liquid reaction medium employed may include any solvent compatible with the catalyst system and may include pure alcohols, or mixtures of the alcohol feedstock and/or the desired carboxylic acid and/or esters of these two compounds. The preferred solvent and liquid reaction medium for the low water carbonylation process comprises the carboxylic acid product. Thus, in the carbonylation of methanol to acetic acid, the preferred solvent is acetic acid.

Water is contained in the reaction medium but at concentrations well below that which has heretofore been thought practical for achieving sufficient reaction rates. It has previously been taught that in rhodium-catalyzed carbonylation reactions of the type set forth in this invention, the addition of water exerts a beneficial effect upon the reaction rate (U.S. Pat. No. 3,769,329). Thus most commercial operations run at water concentrations of at least about 14 wt %. Accordingly, it is quite unexpected that reaction rates substantially equal to and above reaction rates obtained with such high levels of water concentration can be achieved with water concentrations below 14 wt % and as low as about 0.1 wt %.

In accordance with the carbonylation process most useful to manufacture acetic acid according to the present invention, the desired reaction rates are obtained even at low water concentrations by including in the reaction medium methyl acetate and an additional iodide ion which is over and above the iodide which is present as a catalyst promoter such as methyl iodide or other organic iodide. The additional iodide promoter is an iodide salt, with lithium iodide being preferred. It has been found that under low water concentrations, methyl acetate and lithium iodide act as rate promoters only when relatively high concentrations of each of these components are present and that the promotion is higher when both of these components are present simultaneously (U.S. Pat. No. 5,001,259). The concentration of lithium iodide used in the reaction medium of the preferred carbonylation reaction system is believed to be quite high as compared with what little prior art there is dealing with the use of halide salts in reaction systems of this sort. The absolute concentration of iodide ion content is not a limitation on the usefulness of the present invention, only on the improvements in acetic acid production.

The carbonylation reaction of methanol to acetic acid product may be carried out by contacting the methanol feed, which is in the liquid phase, with gaseous carbon monoxide bubbled through a liquid acetic acid solvent reaction medium containing the rhodium catalyst, methyl iodide-type promoter, methyl acetate, and additional soluble iodide salt promoter, at conditions of temperature and pressure suitable to form the carbonylation product. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, can be used provided that the salt is sufficiently soluble in the reaction medium to provide the desired level of the iodide. The iodide salt can be a quaternary salt of an organic or inorganic cation. When the iodide is added as metal salt, preferably it is an iodide salt of a member of the group consisting of the metals of Group Ia and Group IIa of the periodic table as set forth in the "Handbook of Chemistry and Physics" published by CRC Press, Cleveland, Ohio, 1975–76 (56th edition). In particular, alkali metal iodides are useful, with lithium iodide being preferred. In the low water carbonylation process most useful in this invention, the additional iodide over and above the organic iodide promoter is present in the catalyst solution in amounts of from about 2 to about 20 wt %, the methyl acetate is present in amounts of from about 0.5 to about 30 wt %, and the methyl iodide is present in amounts of from about 5 to about 20 wt %. The rhodium catalyst is present in amounts of from about 200 to about 1000 parts per million (ppm).

Typical reaction temperatures for carbonylation will be approximately 150° to about 250° C., with the temperature range of about 180° to about 220° C. being the preferred range. The carbon monoxide partial pressure in the reactor can vary widely but is typically about 2 to about 30 atmospheres, and preferably, about 3 to about 10 atmospheres. Because of the partial pressure of by-products and the vapor pressure of the contained liquids, the total reactor pressure will range from about 15 to about 40 atmospheres.

A typical reaction and acetic acid recovery system which is used for the iodide-promoted rhodium catalyzed carbonylation of methanol to acetic acid is shown in FIG. 1 and comprises a liquid-phase carbonylation reactor 10, flasher 12, and a methyl iodide-acetic acid splitter column 14 which has an acetic acid side stream 17 which proceeds to further purification. The carbonylation reactor 10 is typically a stirred vessel within which the reacting liquid contents are maintained automatically at a constant level. Into this reactor there are continuously introduced fresh methanol, carbon monoxide, sufficient water as needed to maintain at least a finite concentration of water in the reaction medium, recycled catalyst solution (stream 13) from the flasher base, a recycled methyl iodide and methyl acetate phase (stream 30), and an aqueous acetic acid phase (stream 32) from the overhead receiver decanter 22 of the methyl iodide-acetic acid splitter column 14. Alternate distillation systems can be employed so long as they provide means for recovering the crude acetic acid and recycling catalyst solution, methyl iodide, and methyl acetate to the reactor. In a preferred process, carbon monoxide is continuously introduced into the carbonylation reactor 10 just below the agitator which is used to stir the contents. The gaseous feed is, of course, thoroughly dispersed through the reacting liquid by this means. A gaseous purge stream is vented from the reactor to prevent buildup of gaseous by-products and to maintain a set carbon monoxide partial pressure at a given total reactor pressure. The temperature of the reactor is controlled automatically, and the carbon monoxide feed is introduced at a rate sufficient to maintain the desired total reactor pressure.

Liquid product is drawn off from carbonylation reactor 10 at a rate sufficient to maintain a constant level therein and is introduced to flasher 12 via line 11. In flasher 12 the catalyst solution is withdrawn as a base stream 13 (predominantly acetic acid containing the rhodium and the iodide salt along with lesser quantities of methyl acetate, methyl iodide, and water), while the overhead 15 of the flasher comprises largely the product acetic acid along with methyl iodide, methyl acetate, and water. Dissolved gases in stream 11 consisting of a portion of the carbon monoxide along with gaseous by-products such as methane, hydrogen, and carbon dioxide exit the flasher through stream 15 to the splitter column 14, then to the splitter column overhead receiver decanter 22 via stream 33, and exits the system through a vent shown as line 24 on the top of the overhead receiver decanter 22. The overhead 20 from methyl iodide, acetic acid splitter column comprising mainly methyl iodide and methyl acetate plus some water, acetic acid and volatiles is normally recycled via line 21 to the carbonylation reactor 10.

The product acetic acid drawn from the side of methyl iodide-acetic acid splitter column 14 near the base (it can also be withdrawn as a base stream 18 with a portion of this product acetic acid recycle to 12 via line 16) is directed via line 17 for final purification, such as to remove water, as desired, by methods which are known to those skilled in the art including, most preferably, distillation.

Provided sufficient water is present, when overhead 20 is condensed it typically splits into two liquid phases in overhead receiver decanter 22. The heavy phase 30 is comprised mainly of methyl iodide plus some methyl acetate and acetic acid as well as the alkane and carbonyl impurities. The light phase 32 is comprised mainly of water and acetic acid plus some methyl acetate and carbonyl impurities. A slip stream portion of the heavy phase 30 from methyl iodide-acetic acid splitter may then be subject to treatment and the remaining stream can be combined with the light phase 32 and with recycle products from other further purification processes containing methyl iodide, methyl acetate, water, and other impurities to become recycle 21.

In accordance with the process of aforementioned EP 487,284, carbonyl impurities which accumulate in the methyl iodide-rich heavy phase 30 or in the total overhead 20 (if it does not separate into two phases) are removed from this stream in the carbonylation process to yield a substantial improvement in acetic acid product quality. Thus, the methyl iodide-rich phase 30 which contains carbonyl impurities such as acetaldehyde, crotonaldehyde, butyraldehyde, and the like, is reacted with a compound which converts the carbonyl impurities to derivatives which can be separated from the reaction product by distillation to provide a recycle stream free from carbonyl impurities. In the preferred embodiment, the methyl iodide-rich phase is treated with an aqueous amino compound. A subsequent separation is carried out to remove the volatile overhead from the non-volatile amine residues.

It has now been found that the vent gas stream 24 from overhead receiver decanter 22 contains a substantially higher concentration of carbonyl compounds relative to the methyl iodide-rich phase 30; carbonyl compounds such as acetaldehyde. Previous to this invention, heavy phase 30 was treated to remove carbonyl compounds by the process set forth in EP 487,284. At the time of the invention disclosed in EP 487,284, the higher concentration of carbonyl impurities in the vent gas condensate was not recognized. Accordingly, the treatment disclosed in EP 487,284 did not take advantage of the higher concentration of carbonyls in the vent gas condensate stream. It has now been discovered that the concentration of for example, acetaldehyde, is approximately two times or more as great in the vent gas condensate stream 24 than the heavy phase stream 30.

From the top of the receiver 22, vent gas is removed via line 24. The vent gas includes noncondensable light gases such as carbon monoxide, carbon dioxide, methane, hydrogen as well as condensable materials such as methyl iodide, methyl acetate and carbonyl materials including acetaldehyde. The gases are vented from receiver 22 via line 24 and chilled to a temperature sufficient to condense and separate the condensable methyl iodide, methyl acetate, acetaldehyde and other carbonyl components and directed to vessel 70 shown in FIG. 2. As mentioned previously, stream 24 contains a highly concentrated level of acetaldehyde relative to the heavy phase stream 30. For example, it has been found that stream 24 contains approximately 1.3 wt % acetaldehyde whereas stream 30 contains approximately 0.5% acetaldehyde. Typically, the volume of stream 24 is less than about 10 vol % of the heavy phase 30 being treated for carbonyl compound removal. Thus, in one aspect of this invention, the condensable stream 24 is directed to processing to remove the carbonyl compounds therefrom.

Leaving overhead receiver decanter 22 is also the heavy phase stream 30. In another aspect of the present invention, a slip steam 34, generally a small amount, e.g., less than about 25 vol %, preferably, less than about 20 vol %, of heavy phase 30 may also be directed to the carbonyl treatment process of this invention and the remainder recycled to the reactor via line 21. The light phase 32 separated in overhead receiver decanter 22 is recycled to the reactor via line 21.

In yet another aspect of this invention, condensable material from stream 24 and stream 34 may be combined and treated to remove carbonyl compounds therefrom.

Figure 2:
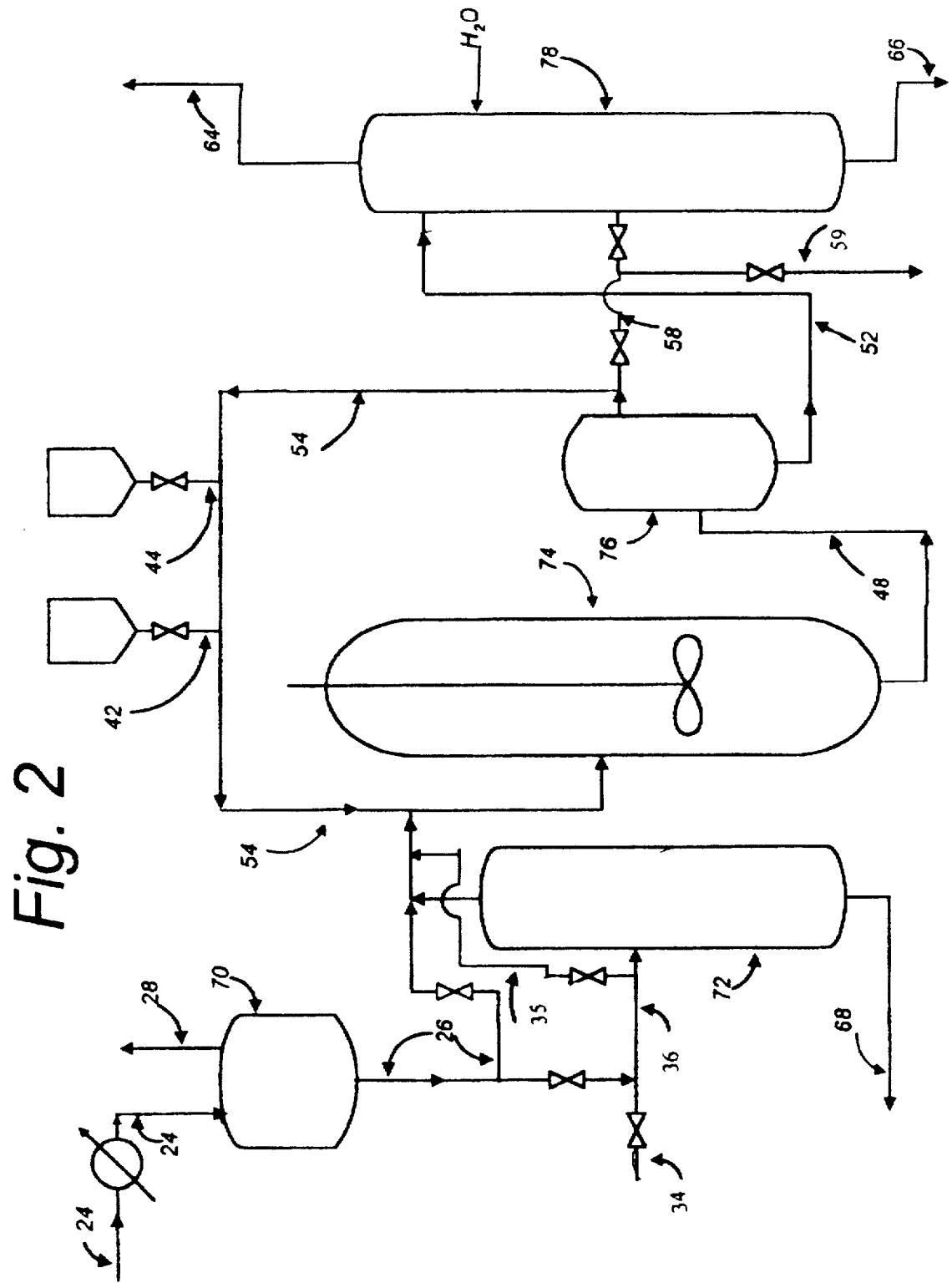
FIG. 2 illustrates a preferred embodiment for the removal of carbonyl impurities form acetic acid formed by a carbonylation reaction.

The separation of the methyl iodide from the impure nitrogenous reaction product can be more readily described by referring to FIG. 2. It is to be understood that any reactive amino compound is useful in the process of this invention and, thus, the description herein is not intended to limit the invention. From FIG. 2, it can be seen that entering overhead receiver vessel 70, is chilled recycle stream 24 which is ultimately fed to reactor 74. Hydroxylamine sulfate (HAS) feedstream 42, and sodium hydroxide feedstream 44, as well as condensed material from gas stream 26 are also fed to reactor 74. Exiting vessel 70 are the condensable materials of stream 24, now stream 26. Tower 72 serves to remove alkanes and acetic acid. The bottoms 68 of tower 72 comprise alkane waste and are directed to further treatment. The reaction of carbonyl impurities with hydroxylamine to form oximation products and the corresponding sulfate salts takes place in reactor 74. The oximation and salt products are soluble in the aqueous phase of the reactor provided adequate temperature and/or water concentration are maintained. To ensure formation of the oximation products, intimate contact and mixture of the carbonyl impurities and hydroxylamine is recommended. The reactor may be of any suitable equipment known in the art including a stirred, back-mix, or plug flow reactor.

The condensable materials from stream 24 (now stream 26) are separated in vessel 70 from the noncondensable light gases stream 28. The light gases 28 may be directed to further scrubbing action to remove any condensable iodide and methyl acetate therefrom. Condensable material including a major amount of methyl iodide and smaller amounts of acetaldehyde and methyl acetate are directed for the further processing of this invention to remove the acetaldehyde and other carbonyl compounds therefrom.

In various aspects of the present invention, streams containing carbonyl impurities may be directed to the tower 72 and then to the reactor 74, or the tower 72 may be bypassed and streams be directed solely to the reactor 74. Streams may be combined or fed individually into either the tower or the reactor. For illustrative purposes herein, HAS and sodium hydroxide are added for treatment of the carbonyl impurities via line 54.

26+34 TO TOWER THEN REACTOR

In a preferred process of the present invention, the condensed material of stream 26 is combined with slip stream 34 (the combined stream illustrated in FIG. 2 as stream 36) and is directed to tower 72. Upon exiting tower 72, stream 36 is then contacted with an amino compound via line 54 and directed to reactor 74, and further processed. As an option not illustrated in FIG. 2, instead of combining streams 26 and 34 to form stream 36, each stream may be fed individually to tower 72 and processed further.

26+34 TO REACTOR (NO TOWER)

An alternate process involves directing stream 36 to reactor 74 via line 35 (bypassing tower 72). Similar to the option above, streams 26 and 34 may be individually fed to reactor 74. The stream is then treated with an aqueous amino compound as described herein and further processed.

34 TO TOWER & THEN REACTOR

Another alternate process involves directing stream 34 (no combining with stream 26) to tower 72 for alkane and acetic acid removal, and then contact with an aqueous amino compound as described above and further processed.

34 TO REACTOR (NO TOWER)

Yet another alternate process involves bypassing tower 72 and directing stream 34, via line 35, to reactor 74. The stream is then treated with an aqueous amino compound as described and further processed.

26 TO TOWER & THEN REACTOR

Still another alternative process involves directing stream 26 only (no combining with stream 34) to tower 72 and then to treatment with an aqueous amino compound as described above and further processed.

26 TO REACTOR (NO TOWER)

A still further alternate process of the present invention involves directing stream 26 only (again, no combining with stream 34) into reactor 74 (bypassing tower 72) and then to treatment with an aqueous amino compound as described above and further processed. Optionally, stream 34 may be processed in column 72 and the distillate combined with stream. 26 to be processed as above.

The HAS may be stored in a tank as illustrated and dispersed as necessary via stream 42. Since hydroxylamine as the free base slowly decomposes, it is preferred to use hydroxylamine in its acid salt form. The free hydroxylamine is liberated upon treatment of the acid salt with a base such as potassium hydroxide, sodium hydroxide or lithium hydroxide. If sodium hydroxide is used as the base to liberate the hydroxylamine from its acidic salt, then such liberation also produces the corresponding sodium salt as a byproduct. The HAS is preferably used in an amount of about 1 to about 2 equivalents of starting hydroxylamine per equivalent of the carbonyl impurities which are contained in stream 26. The amount of carbonyl impurities can be determined by analytical methods prior to reaction with an amino compound.

The base used to liberate the free hydroxyl amine may be stored in a tank illustrated in FIG. 2, and dispersed as necessary via stream 44. It is preferably used in an amount of about 0.8 to about 1.0 equivalents per equivalent of starting hydroxylamine so that a small amount of hydroxylamine remains in the form of its acid salt to create a pH buffer. The pH of the reactant solution is maintained in the range of about 4.0 to about 7.0, preferably about 4.0 to about 6.0, and most preferably in the range of about 4.5 to about 5.5. Use of larger amounts of base can cause the pH to rise above 7 and result in the decomposition of the unstable hydroxylamine free base. The free base decomposes to undesirable volatile by-products such as ammonia. This in turn initiates undesirable condensation reactions of the methyl iodide-rich combined recycle streams with the free hydroxylamine which is formed. It has been discovered that by maintaining the pH of the reaction solution at or near about 4.5 the oximation reaction may be maximized, and the methyl iodide undesirable conversion to inorganic iodide may be minimized.

It has also been discovered that at elevated temperatures methyl iodide is converted to inorganic iodide salts; which salts may be lost during processing (e.g. via stream 66). At low temperatures, crystallization has been found to occur. The reaction system must therefore be maintained under temperature and pressure conditions so that the reaction mixture remains in a liquid state. The reaction is generally run at a temperature of about 0° to about 70° C. for a period of from about 1 min. to about 1 hour. The circulating reaction lines, for examples lines 48 and 54, generally need some form of temperature control to avoid crystallization in the lines. Sufficient water is maintained in the reaction process to keep the salts and oximes in solution. The water may be supplied by various means. For example, (1) water may be supplied in the HAS itself, by utilizing a dilute HAS solution, e.g. about 10%, (2) by supplying fresh water to the reaction system, (3) by use of recycled water from the reaction process, or (4) by employing dilute NaOH.

Although an aqueous hydroxylamine salt such as HAS, hydroxylamine hydrochloride, hydroxylamine bisulfate, hydroxylamine acetate, or hydroxylamine phosphate, or the free base form of hydroxylamine is the preferred amino compound for use in the process of this invention, other amino compounds (free base amines or acid salts thereof) are suitable. These amino compounds include but are not limited to aniline and acid salts thereof such as aniline acetate, aniline sulphate, hydrazine, phenylhydrazine and/or their acid salts; alkyl amines such as methylamine, ethylamine, propylamine, phenylamine and naphthylamine. Moreover, in less preferred embodiments, other compounds can be used to treat the splitter column overhead, stream 20, including bisulfite salts, as for example sodium bisulfite.

Reaction of hydroxylamine with carbonyl impurities yields an oxime whereas reaction with hydrazine yields the hydrazone. Regardless of the type of amino compound used, nitrile formation from the reaction product of an aldehyde with an amino compound can result during prolonged heating such as during distillation. The nitrile forming reactions are shown below for (1) oxime products and (2) hydrazone products.

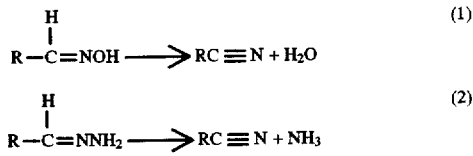

It is necessary to separate the nitrogenous compounds from the methyl iodide before the methyl iodide is returned to the carbonylation reactor. In accordance with the present invention, a series of steps are utilized to provide this separation and yield a purified recycle stream and, in particular, a pure recycle stream which is nitrogen-free. To assist in the separation of the amino compounds from the purified heavy phase product, water in a feed ratio of about 0.1–3 feed volume of water to heavy phase is added to the column (illustrated as tower 78 in FIG. 2) to prevent the formation of nitrile.

After treatment and reaction of the carbonyl impurities with an aqueous amino compound, the reaction products are collected via line 48 from reactor 74 and directed to decanter 76. In decanter 76, the light aqueous phase 54 which contains unreacted hydroxylamine sulfate as well as most of the oximation products from reaction of the carbonyl impurities with the hydroxylamine is separated. The aqueous phase containing the hydroxylamine sulfate may be fully or partially recycled to reactor 74 via line 54. Alternatively, a portion of stream 54 illustrated as stream 58 may be directed to distillation tower 78 for stripping of the methyl iodide. The oximes concentrate in the aqueous phase such that a purge of the formed oximes is necessary. These may be purged directly via stream 59 or purged and fed through stream 58 to recover soluble methyl iodide. The recirculation of the aqueous phase 54 greatly improves pH control which is necessary to release the hydroxylamine from the hydroxylamine salt and allows optimum reaction with the carbonyl impurities. The organic phase 52 containing methyl iodide, minor amounts of water, as well as trace amounts of hydroxylamine sulfate, oximes and impurities which separate from the aqueous hydroxylamine sulfate phase 54 is withdrawn from the decanter 76 via line 52 and directed to distillation tower 78 to recover methyl iodide. Upon distillation in tower 78, a distillate containing a purified methyl iodide recycle stream leaves the tower via line 64. This light ends stream 64 may be recycled to the carbonylation process. The bottoms 66 from distillation tower 78 comprise primarily water, the separated oximes, sodium sulfate, unreacted HAS, as well as minor amounts of other impurities such as high boiling point alkanes. Water from a portion of stream 66 may be recycled in the system to preserve water balance.

As has been previously discussed, we have found that oximes such as those formed by reaction of the hydroxylamine and aldehydes, in particular, acetaldehyde oxime can readily convert to the nitrile, e.g., acetonitrile, which has a boiling point close to the methyl iodide-rich recycle 64 and which will distill with and contaminate the recycle phase distillate 64 leaving distillation tower 78. Such conversion occurs more readily under conditions of high temperature. Accordingly, methods to reduce oximes and nitrites are employed. For example, in order to remove oximes and prevent formation of nitrites from distillate 64 leaving distillation tower 78, additional water may be added to the distillation tower 78. The water content is preferably in an amount of about 0.1 to about 3 feed volume ratio of water to organic phase 52 (tower) feed. The water partitions the oxime to the bottom of distillation tower 78, and reduces the temperature needed for distillation, further reducing the undesirable nitrile formation.

We claim:

1. In a process for the carbonylation of methanol to a product of acetic acid, said methanol is carbonylated in a reaction medium containing a Group VIII metal catalyst, an organic iodide, and iodide salt promoter; the products of said carbonylation separated into a volatile phase comprising product and a less volatile phase comprising Group VIII metal catalyst, acetic acid, iodide catalyst promoter, and organic iodide; said product phase distilled in a distillation tower to yield a purified product and an overhead organic iodide, methyl acetate, water, acetic acid, and unreacted methanol, and recycling said overhead to said carbonylation reactor, the improving consisting of:

(a) directing at least a portion of the overhead to an overhead receiver which separates the overhead into a light phase, comprising acetic acid and water, and a heavy phase comprising methyl acetate and organic iodide;

(b) venting a light gas stream from the overhead receiver of (a) to a chiller;

(c) chilling the vented gas stream of (b) under suitable conditions to condense the chilled vented gas stream into a condensed phase and separate in an overhead receiver vessel said condensed phase from noncondensable light gases;

(d) contacting the condensed phase of (c) with an aqueous amino compound which forms water soluble nitrogenous derivatives of carbonyls;

(e) separating out resulting nitrogenous derivatives of carbonyls and returning a purified condensed phase of (c) to the carbonylation reactor.

2. The process of claim 1 wherein prior to (e), a water content is provided to a distillation tower which recovers purified heavy phase product in an amount of about 0.1 to about 3 feed volume ratio of water to organic phase.

3. The process of claim 1 wherein a portion of the heavy phase of (a) and a least a portion of the condensed phase of (c) are contacted with an aqueous amino compound which forms water soluble nitrogenous derivatives.

4. The process of claim 3 wherein the heavy phase and the condensable phase are contacted with an amino compound individually.

5. The process of claim 3 wherein the heavy phase and the condensable phase are contacted as a combined stream with an amino compound.

6. The process of claim 1 wherein a portion of the heavy phase of (a) and at least of portion of the condensed phase of (c) are (1) directed to treatment to remove alkanes and acetic acid and then (2) contacted with an aqueous amino compound which forms water soluble nitrogenous derivatives.

7. The process of claim 1 wherein said organic iodide catalyst promoter is methyl iodide.

8. The process of claim 1 wherein said amino compound is hydroxyl amine and said nitrogenous derivatives are oximes.

9. The process of claim 8 wherein the amino compound comprises a hydroxylamine acid salt and a base is supplied to the carbonylation reaction to liberate said hydroxylamine from said salt.

10. The process of claim 9 wherein the hydroxylamine acid salt is selected from the group consisting of hydroxylamine sulfate, hydroxylamine hydrochloride, hydroxylamine bisulfate, hydroxylamine acetate, hydroxylamine phosphate, or the free base form of hydroxylamine.

11. The process of claim 8 wherein the amino compound is selected from the group consisting of aniline acetate, aniline sulphate, hydrazine, phenylhydrazine, methylamine, ethylamine, propylamine, phenylamine, naphthylamine, and acid salts thereof.

12. The process of claim 9 wherein the base is selected from the group consisting of sodium hydroxide, potassium hydroxide, and lithium hydroxide.

13. The process of claim 1 wherein said carbonyl impurities present in said overhead comprise acetaldehyde, crotonaldehyde, butyraldehyde, 2-ethyl crotonaldehyde, and 2-ethyl butyraldehyde.

* * * * *